(12) United States Patent
Kuiper et al.

(10) Patent No.: US 10,905,546 B1
(45) Date of Patent: Feb. 2, 2021

(54) CONTROLLED UNFOLDING OF INTRAOCULAR LENSES

(71) Applicant: Verily Life Sciences LLC, Mountain View, CA (US)

(72) Inventors: Stein Kuiper, Pacifica, CA (US); Brooke Basinger, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 164 days.

(21) Appl. No.: 16/122,741

(22) Filed: Sep. 5, 2018

Related U.S. Application Data

(60) Provisional application No. 62/554,775, filed on Sep. 6, 2017.

(51) Int. Cl.
*A61F 2/16* (2006.01)

(52) U.S. Cl.
CPC .... *A61F 2/1662* (2013.01); *A61F 2002/1681* (2013.01); *A61F 2210/0038* (2013.01); *A61F 2250/0001* (2013.01)

(58) Field of Classification Search
CPC combination set(s) only.
See application file for complete search history.

(56) References Cited

U.S. PATENT DOCUMENTS

| 4,666,445 | A | 5/1987 | Tillay |
| 7,491,350 | B2 * | 2/2009 | Silvestrini ........... C23C 14/0005 164/46 |
| 7,976,577 | B2 * | 7/2011 | Silvestrini ................ G02C 7/02 623/5.13 |
| 2011/0264103 | A1 | 10/2011 | Cole et al. |
| 2014/0094908 | A1 | 4/2014 | Zaldivar et al. |

FOREIGN PATENT DOCUMENTS

WO 2008/091859 A1 7/2008

OTHER PUBLICATIONS

Krader, Cheryl G., "Warm Viscoelastic Hastens IOL Unfolding", Ophthalmology Times, Jun. 1, 2015, 2 pages.
Devgan, Uday, MD, "Warming Viscoelastics, Lens Implants Can Be Beneficial", Ocular Surgery News U.S. Edition, Aug. 25, 2010, 5 pages.

* cited by examiner

*Primary Examiner* — Vi X Nguyen
(74) *Attorney, Agent, or Firm* — Christensen O'Connor Johnson Kindness PLLC

(57) ABSTRACT

A method for controlled unfolding of an intraocular lens (IOL) includes inserting a folded IOL into an eye and heating a shape memory alloy (SMA) ring included with the IOL to a temperature that is at least a transition temperature of the SMA ring. The transition temperature is above a body temperature. Heating the SMA ring causes the SMA ring to unfold the IOL.

24 Claims, 7 Drawing Sheets

CONTROLLED UNFOLDING OF INTRAOCULAR LENSES

CROSS-REFERENCE TO RELATED APPLICATION

This application claims the benefit of U.S. Provisional Application No. 62/554,775, filed Sep. 6, 2017, which is hereby incorporated by reference in its entirety.

TECHNICAL FIELD

This disclosure relates generally to implantable ophthalmic devices, and in particular but not exclusively, relates to the controlled unfolding of implantable intraocular lenses.

BACKGROUND INFORMATION

Implantable optical devices may be constrained in size by conventional surgical techniques. For example, eye incisions may desirably be limited to mm length incisions, 2 to 5 mm for example. The small incisions, however, may preclude or limit the implantation of bulky ophthalmic devices, or at least cause the physician to limit their recommendation. As such, implantation of intraocular devices that include multiple components and electronics may be limited due to their bulkier size over conventional intraocular devices. While fabrication techniques may allow some reduction in size of such intraocular devices, the manipulation of the devices during implantation, such as unfolding and/or unrolling, may promote undesirable movement in the eye if the unfolding/unrolling is fast and/or uncontrolled. Such movement may damage delicate eye structures as well. As such, it may be desirable to provide an intraocular device that includes components that unroll/unfold in a slow and controlled fashion.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
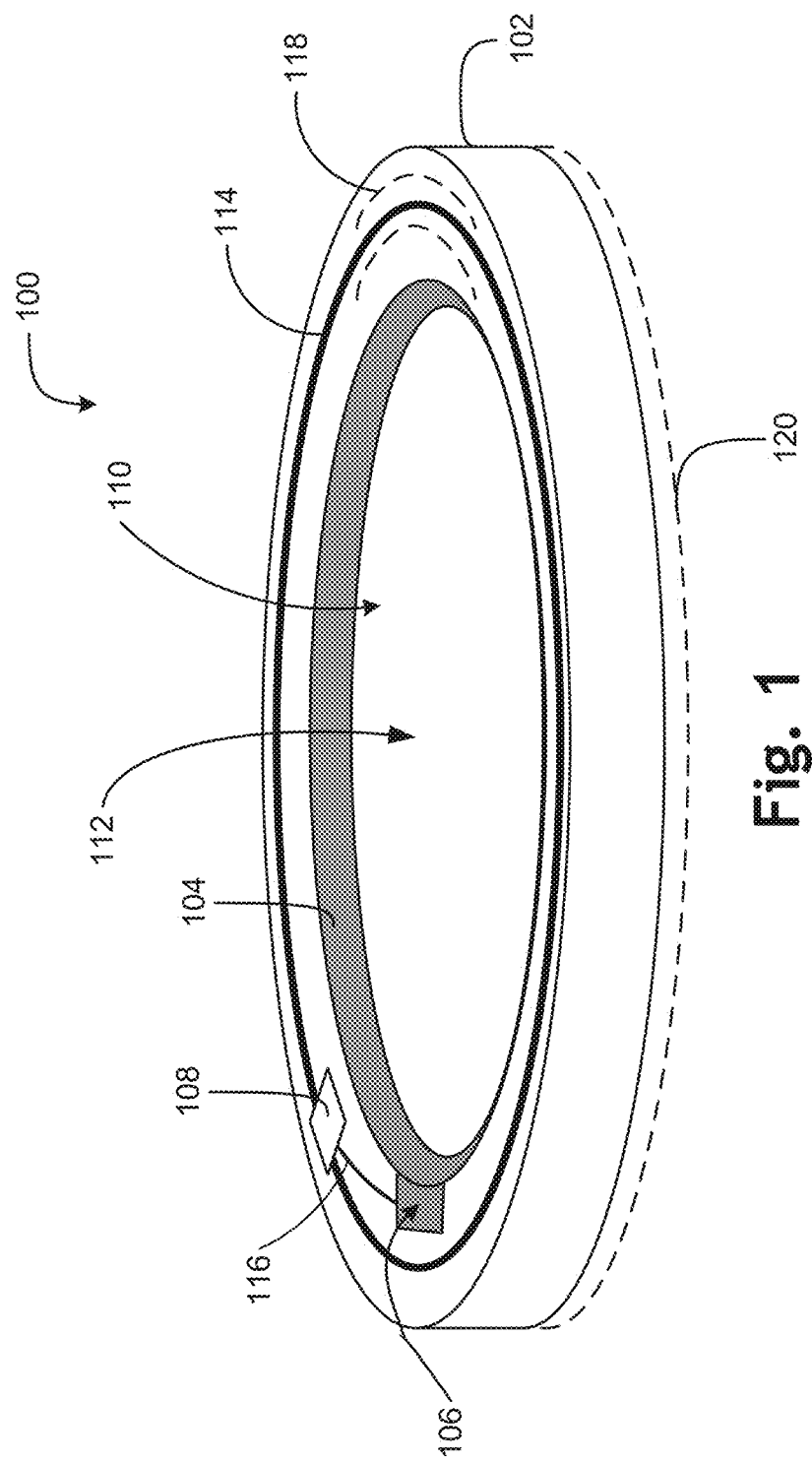
FIG. 1 is a perspective view of an IOL 100 including one or more shape memory alloy (SMA) rings in accordance with an embodiment of the disclosure.

Embodiments of a system and method for implantable intraocular lenses (IOLs) having a slow and controlled unfolding are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Smart" intraocular lenses (IOLs) are implantable ophthalmic devices that include electronics that perform a variety of tasks. For example, some smart IOLs may include dynamic optics that provide accommodation to a user. The dynamic optic may be based on liquid crystal (LC) or electrowetting techniques, for example. LC-based IOLs may include one or more layers of LC-material contained between optical elements that may include electrodes and diffractive optics, for example. The LC-based IOLs, as such, require a protective enclosure to contain the LC-material within the IOL and to prevent leakage into the user's eye. IOLs based on electrowetting techniques likewise are conventionally encased in an enclosure. The electrowetting IOLs further included two immiscible liquids, such as an oil and a saline, that provide a dynamic optic via a deformable refractive interface formed between the two liquids. In addition to the dynamic optic components, both types of IOLs further include electronics and power sources that control and power the dynamic optic. Accordingly, the IOLs, in at least part due to the dynamic optic and the controlling electronics, may become somewhat bulky, especially compared with conventional static IOLs.

The implantation of the IOLs may put constraints on their size, area and/or volume, however. Conventional static IOLs may be implanted using incisions that range from 2 to 5 mm in length (based on current surgical techniques), but bulkier IOLs may not fit through a 5 mm incision. As such, eye care physicians may be less inclined to use them. Further, if the IOLs are folded and/or rolled up to fit through an incision that is 5 mm or less in length, the process of folding/rolling and unfolding/unrolling may cause defects and/or device failure. For example, electronic interconnects may be damaged or broken leading to device failure. Or, an IOL enclosure may burst allowing the exchange of fluids between the eye and the device, which may lead to malfunction or failure of the IOL. Additionally, the process of unfolding/unrolling the IOLs may damage delicate eye structures if the unrolling/unfolding is not implemented in a slow and/or controlled manner. Accordingly, it may be desirable for IOLs to include a feature that allows the unfolding to be initiated and controlled so to avoid or reduce the risk of internal eye damage.

One solution may be to include a feature in an IOL that can unfold/unroll in a slow and controlled manner in response to control energy. For example, a shape memory alloy (SMA) ring may be embedded in the IOL, which is folded up prior to implantation and which only unfolds after being heated to a transition temperature. The heating may be controlled so that the temperature of the SMA ring slowly increases from a starting transition temperature to a final transition temperature. The heating of the SMA ring from the starting to the final transition temperatures will cause the SMA ring to completely unfold to a desired geometry, and may also cause the SMA ring to change from a martensite phase to an austenite phase. In the austenite phase, the SMA ring may remain in the desired geometry. Additionally, the heating energy may be provided in a manner to cause the SMA ring to slowly unfold, which allows the physician to monitor the unfolding progress, and to possibly adjust the IOL within the eye as it unfolds. The heating energy may be wirelessly provided through conductive heating, laser pulses, ultrasound, electric heating, rinsing with warm saline, or the like.

FIG. 1 is a perspective view of an IOL 100 including one or more SMA rings in accordance with an embodiment of the disclosure. The illustrative embodiment of the IOL 100 includes a support structure 102, an electrode 104, a contact pad 106, control electronics 108, a dynamic optic 112, an antenna 114, a conductor 116, an SMA ring 118, and an optical window 120. An additional optical window may also be included but is not shown in FIG. 1 (see FIG. 2 for an example). While not shown, the IOL 100 may also be enclosed in a transparent or semitransparent biocompatible material. As noted above, the IOL 100 may be rolled up and/or folded for insertion into a user's eye, and the IOL 100 may desirably return to a straight and stretched, e.g., taut, state after unrolling/unfolding. To ensure that the IOL 100 unfolds in a slow and controlled manner, the SMA ring may be slowly heated to a transition temperature, which may be above body temperature. As the temperature of the SMA ring increases above the transition temperature, the SMA ring may begin to unfold and the rate of temperature increase may be controlled to control a rate of unfolding.

The support structure 102 may provide mechanical support for the various features of the IOL 100. For example, the support structure 102 may provide support for the electrode 104, the contact 106, the control electronics 108, the dynamic optic 112, the optical window 120, the conductor 116, the antenna 114, the SMA ring 118, and various other components discussed herein. In some embodiments, however, some of the components, such as the control electronics 108, the conductor 116, the antenna 114, and the contact 106 may be disposed on a separate substrate (not shown), which may then be disposed on a surface of the support structure 102 or embedded within the support structure 102. In some embodiments, the SMA ring 118, which is included with the support structure 102, provides the substrate for mounting of the various electronic components. Of course, other arrangements are possible and the SMA ring 118 may not function as a substrate for the electronic components.

In general, the support structure 102 may be formed from a biocompatible material that is amenable to implantation into an eye. Example materials may include silicones, sol-gels, and AcrySof®. Other biocompatible materials, such as biocompatible hydrogel, hydrophobic acrylic, fluorinated polymethacrylate and/or the like, may also be used. The support structure 102 may be a main structural component of the IOL 100 that provides a platform for other IOL 100 components. The support structure 102 may be flexibly capable of being rolled up and/or folded so that it may be manipulated into a smaller shape to accommodate insertion into an eye through a small incision, e.g., an incision roughly 2 mm in length. The support structure 102 is preferably highly elastic, so that it will return to its original shape after unrolling/unfolding. In some embodiments, the support structure 102 can be annulus-shaped, e.g., washer-shaped, having an opening 110, e.g., an aperture, formed there through. The opening 110 may provide an optical path for the IOL 100. In such embodiments, the optical window 120 is placed over at least the opening 110 on one side of the support structure 102, and a second optical window may be disposed over the opening 110 on the other side of the support structure 102.

The opening 110 may be formed by an inner surface, e.g., a sidewall, of the support structure 102. In some embodiments, the sidewall may be at a non-orthogonal angle, e.g., an oblique angle, to top and/or bottom surfaces, e.g., surfaces 224 and 226, of the support structure 102. For example, the sidewall may be at a 45° angle to at least one of the top or bottom surfaces of the support structure 102. In general, the type of dynamic optic 112 of the IOL 100 may determine a slope or angle of the sidewall with respect to a top or bottom surfaces of the support structure 102. Other angles other than 45° are within the scope of the present disclosure. For example, an electrowetting-based dynamic optic, such as the illustrated dynamic optic 112, the sidewall may be at an oblique angle, and may be in the shape of a conical frustum in some embodiments. However, if the dynamic optic is based on liquid crystal technology, then the angle of the sidewall may be orthogonal to the top and bottom surfaces of the support structure 102.

In the illustrated embodiment, the electrode 104 may be disposed on the sidewall, and may generally conform to the shape of the sidewall. For example, if the sidewall is shaped as a conical frustum, then the electrode 104 may similarly shaped. In some embodiments, the electrode 104 may have one or more dielectric layers disposed over that assist with implementing the electrowetting technology. For example, charge provided to the electrode, which may form a potential difference with a polar liquid, may alter the surface energy of the overlying dielectric. The altered surface energy, in turn, may cause a meniscal interface to move up or down the electrode, which provides lensing to the IOL 100. In general, the electrode 104 may be formed from a flexible, conductive material that is amenable to being rolled and unrolled without experiencing inelastic deformation. For example, the electrode 104 may be formed from a superelastic alloy, a shape memory alloy, a flexible alloy mesh, or the like.

The contact pad 106 may electrically couple the control electronics 108 to the dynamic optic 112, and may be disposed on a surface of the support structure 102, or a substrate embedded in the support structure. In some embodiments, the contact pad 106 may be part of the electrode 104. However, the contract pad 106 does not need to be part of the electrode, and may be a separate component. Additionally, the contact pad 106 may be coupled to the control electronics via one or more conductors 116. The control electronics 108 may be coupled to at least provide a voltage to the dynamic optic 112. In the illustrated embodiment, the control electronics 108 are coupled to the dynamic optic 112 via the conductor 116, the contact pad 106 and the electrode 104.

The antenna 114 may be formed into a loop around the aperture 110, and may be coupled to the control electronics 108. The antenna 114 may allow for wireless communication between the IOL 100 and an external reader, for example, and in some embodiments may also allow for wireless charging of onboard power sources. In some embodiments, the antenna 114 may be formed from a superelastic metal alloy, and may be the SMA ring 118 in other embodiments of the IOL 100.

The SMA ring 118 may be formed into an annular shape and sized to encompass the aperture 110. In some embodiments, the SMA ring may have an inner diameter of 6 mm, an outer diameter of 7 mm, and a thickness of 100 to 200 microns, but of course other dimensions are possible. The SMA ring 118 may further be sized to fit on a top or bottom surface of the support structure 102, or fit within the support structure 102. For example, the SMA ring 118 may be embedded in the support structure 102. It may be desirable that the SMA ring 118 is formed from a strong yet flexible material that can withstand being folded/rolled to a radius of around 1 mm, but return to a desired shape upon unfolding/unrolling. Additionally, the SMA ring 118 may desirably be strong enough to force the soft components of the IOL 100, such as the support structure 102 and the optical windows, into a desired tautness and straightness to achieve a desired optical quality. The SMA ring 118 may be included in various locations in the IOL 100. For example, the SMA ring 118 may be embedded in the support structure 102 as a reinforcement ring, it may form the electrode 104, or form the antenna 114, and the like.

Accordingly, the SMA ring 118 may be formed from a superelastic alloy such as Nitinol (nickel-titanium alloy) of various compositions, copper-zinc-aluminum, copper-aluminum, copper-aluminum-nickel, or copper-aluminum-beryllium. In some embodiments, the Nitinol may be in an annealed, shape set form that allows it to fold back completely after unfolding. Alternatively, the Nitinol may be in a body temperature shape memory alloy composition that allows it to be folded at room temperature and kept in that shape until it is inserted into the eye where it unfolds due to the surrounding body temperature. In some embodiments, the SMA ring 118 may be of a composition that has a transition temperature above body temperature, 40° C. for example, so that after being folded, the SMA ring will be remain folded until being heated above the transition temperature. And by having the transition temperature above boy temperature, the SMA ring may not begin unfolding just by being implanted into the eye. Additionally, the SMA ring may be encased in an elastomeric support that limits heat conduction from the SMA ring to the surrounding eye environment so that the temperature of the eye stays within an acceptable limit. For example, if the SMA ring is heated to 110° C., the limited heat conduction of the elastomeric support structure may limit the heating of the intraocular liquid to below 50° C. The unfolding of the SMA ring, and ultimately the IOL 100, may be performed using induction heating. By controlling the induction power, the time and speed of the unfolding may be well controlled.

Figure 2:
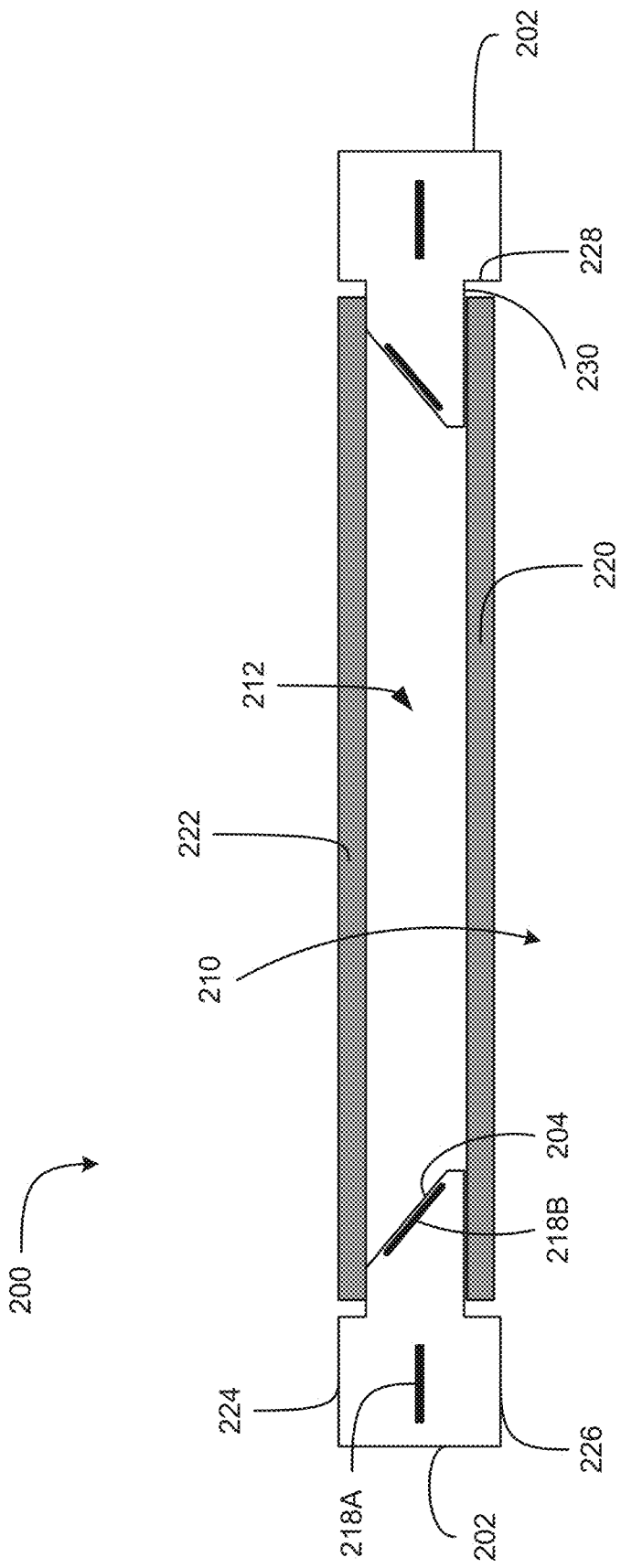
FIG. 2 is a cross-sectional illustration of a portion of an IOL 200 including an SMA ring in accordance with an embodiment of the present disclosure.

FIG. 2 is a cross-sectional illustration of a portion of an IOL 200 including an SMA ring in accordance with an embodiment of the present disclosure. The IOL 200 may be an example of the IOL 100. The IOL 200 includes a support structure 202, an electrode 204, a dynamic optic 212, optical windows 220 and 222, and an SMA ring 218. The SMA rings 218A and 218B show two possible locations for including the SMA ring in the IOL 200. Of course other locations for the SMA ring 218 are within the scope of the present disclosure, and the examples disclosed herein are non-limiting. The SMA ring 218 may be used to unfold the IOL 200 in a slow and controlled manner based on induction heating, which may be provided after implantation of the IOL.

The support structure 202 provides mechanical support for the various other components of the IOL 200. Similar to the support structure 102, the support structure 202 may be formed into an annular shape and may be composed of a biocompatible, soft material. The support structure 202 is amenable to being folded/rolled and unfolded/unrolled without experiencing any damage. The support structure 202 may be molded from a desired material, such as silicones, sol-gels, and AcrySof®, and the various other components, such as the electronics and the SMA ring 218, may be embedded within the support structure 202. The electronics in the IOL 200 refer to control electronics, conductors, contact pads, an antenna, and the electrode 204.

The support structure 202 may further have a recess formed on an inner edge on both the top and bottom surfaces 224, 226 that encircles the aperture 210. The recesses may provide a surface for mounting and sealing the optical windows 220, 222 to the support structure 102. The recess may be defined by surfaces 228 and 230 formed into the bottom surface 226, which may be mirrored on the top surface 224. In some embodiments, the recess formed into the top surface 224 and the recess formed into the bottom surface 226 may be different and provide different surface areas of the support structure 202. Of course, the support structure 202 may be formed without the surfaces 228 and 230 and the optical windows 220 and 222 may, instead, be disposed on the top and bottom surfaces 1224 and 226, respectively.

The electrode 204 may be disposed on or in an inner sidewall of the support structure 202. The electrode 204 may be formed from a flexible conductor, and may be formed from a superelastic alloy in some embodiments. The electrode 204 may be coupled to control electronics and provided a voltage to manipulate the dynamic optic 212.

The dynamic optic 212 may be arranged in an aperture 210 of the support structure 202, and may be coupled to control electronics via the electrode 204. In some embodiments, the dynamic optic 212 may be based on electrowetting technology, which includes two immiscible fluids (one is a polar liquid) enclosed in the aperture 210 and the optical windows 220 and 222. By changing a potential difference between the electrode 204 and the polar liquid, the interface may move up and down the electrode 204, thereby changing an optical power of the dynamic optic 212.

The optical windows 220, 222 may be mounted to top and bottom sides of the support structure 202. The first and second optical windows 220, 222 may be formed from transparent or partially transparent polymerics or thin glass. Example polymerics include Polydimethylsiloxane, hydrophobic acrylic (e.g., AcrySof), silicones, acrylics, epoxies, urethanes, combinations thereof, and the like. While top and bottom are used herein to discuss the opposite sides of the support structure 202, the top and bottom designations do not notate any directionality to the IOL 200 and are used merely as a reference with respect FIG. 2.

The optical windows 220, 222 may be transparent and disposed to cover the aperture 210. The optical windows 220, 222 may be with or without optical power. In some embodiments, one or both of the optical windows provides static optical power to the IOL 200, which may be affected by the dynamic accommodation of the IOL 200. In some embodiments, the optical windows 220, 222 do not have any optical power. In either embodiment, the optical windows 220, 222 may be coupled to the support structure 102 to retain the two immiscible fluids within the cavity formed by the support structure 202 and the optical windows 220, 222.

Additionally, one or both of the optical windows may be conductive. For example, the optical window 220 and/or 222 may be conductive. A transparent conductor, such as indium tin oxide (ITO) may be deposited on the optical windows 118 and/or 120, for example. Having one or both of the optical windows conductive may allow a potential difference to be applied to the dynamic optic 112 for causing changes in accommodation.

As noted above, the SMA ring 218 may be formed from a superelastic alloy, such as Nitinol. Depending on the superelastic alloy implemented, the SMA ring 218 may be of varying thicknesses. For example, if the SMA ring is formed from Nitinol, the SMA ring 218 may be from 25 to 200 microns in thickness. Such thickness may provide the strength to ensure the IOL 200 is stretched and straightened after unrolling/unfolding to mitigate any warpage present in the optical windows and/or the support structure. Of course, other superelastic alloys at different thicknesses are also possible. Additionally, the thickness of the SMA ring 218 may be thick enough so that the SMA ring 218 causes the soft materials to unfold when the SMA ring 218 is being unfolded. Alternatively, the SMA ring 218 may be formed from multiple SMA rings arranged in a stack and separated by one or more elastomeric materials, silicone for example.

An SMA ring 218A may be embedded in a main portion of the support structure 202. The SMA ring 218A may be larger than the aperture 210 and encompass the aperture 210. In some embodiments, the SMA ring 218A may also be a substrate for the various electronics of the IOL 200, such as the control electronics, the antenna, and such. In other embodiments, the SMA ring 218A may not double as a substrate, but provide a reinforcement ring to the IOL 200 so that the IOL is straightened after unfolding. Alternatively, the SMA ring 218A may double as the antenna, such as the antenna 114.

An SMA ring 218B may be embedded adjacent to the sidewall of the support structure 202 and underneath the electrode 204. In such an arrangement, the SMA ring 218 may be formed to conform to a shape of the sidewall. For example, the SMA ring 218B may be formed into a conical frustum shape to conform to the sidewall. However, other shapes are also contemplated, and may be based on the specific design of the support structure 202. Alternatively, the SMA ring 218B may be implemented as the electrode 204 and be electrically coupled to control electronics to drive the dynamic optic 212.

Figure 3:
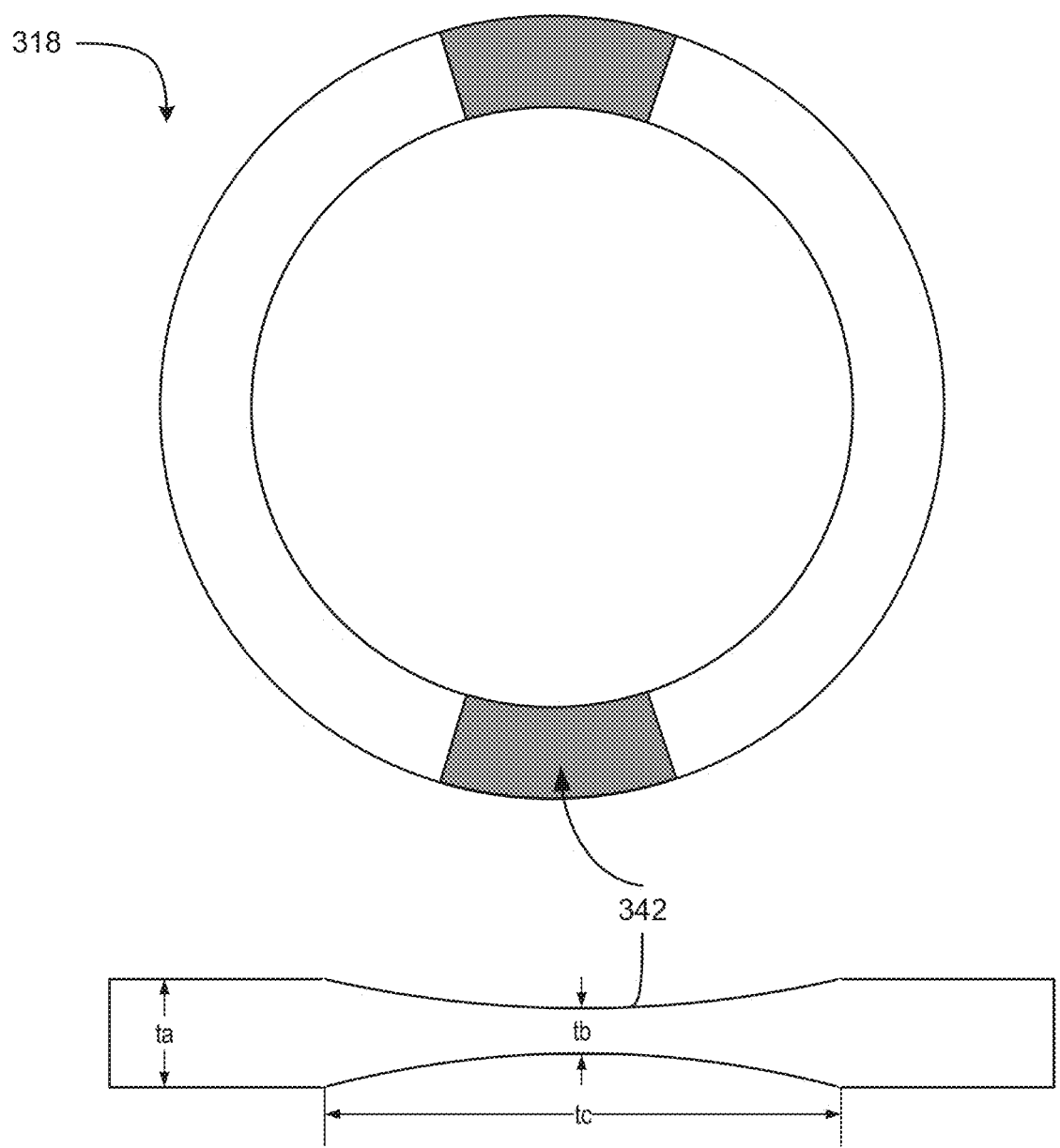
FIG. 3 is an illustrative SMA ring 318 in accordance with an embodiment of the present disclosure.

FIG. 3 is an illustrative SMA ring 318 in accordance with an embodiment of the present disclosure. The SMA ring 318 may be an example of the SMA rings 118 and/or 218. In the illustrated embodiment, the SMA ring 318 may have two folding zones 342 that are thinner than the remainder of the SMA ring 318. While only two folding zones 342 are shown, additional folding zones may be included. For example, the SMA ring 318 may have as many as four or six folding zones. The folding zones 342 may be half the thickness of the remainder of the SMA ring 318, which may provide areas specific for bending/rolling of the SMA ring 318 for the implantation process.

The folding zones 342 may have a thickness tb that, as noted, is thinner than the thickness ta of the rest of the SMA ring 318. While tb may be about half of ta in some embodiments, the relative thickness of tb may be adjusted based on a desired bending radius, material choices, and thickness ta. The folding zones 342 may have a radial length tc, which may be adjusted based on the same factors. The length tc of the folding zone may affect the desired bending radius, and may be adjusted in response.

Figure 4:
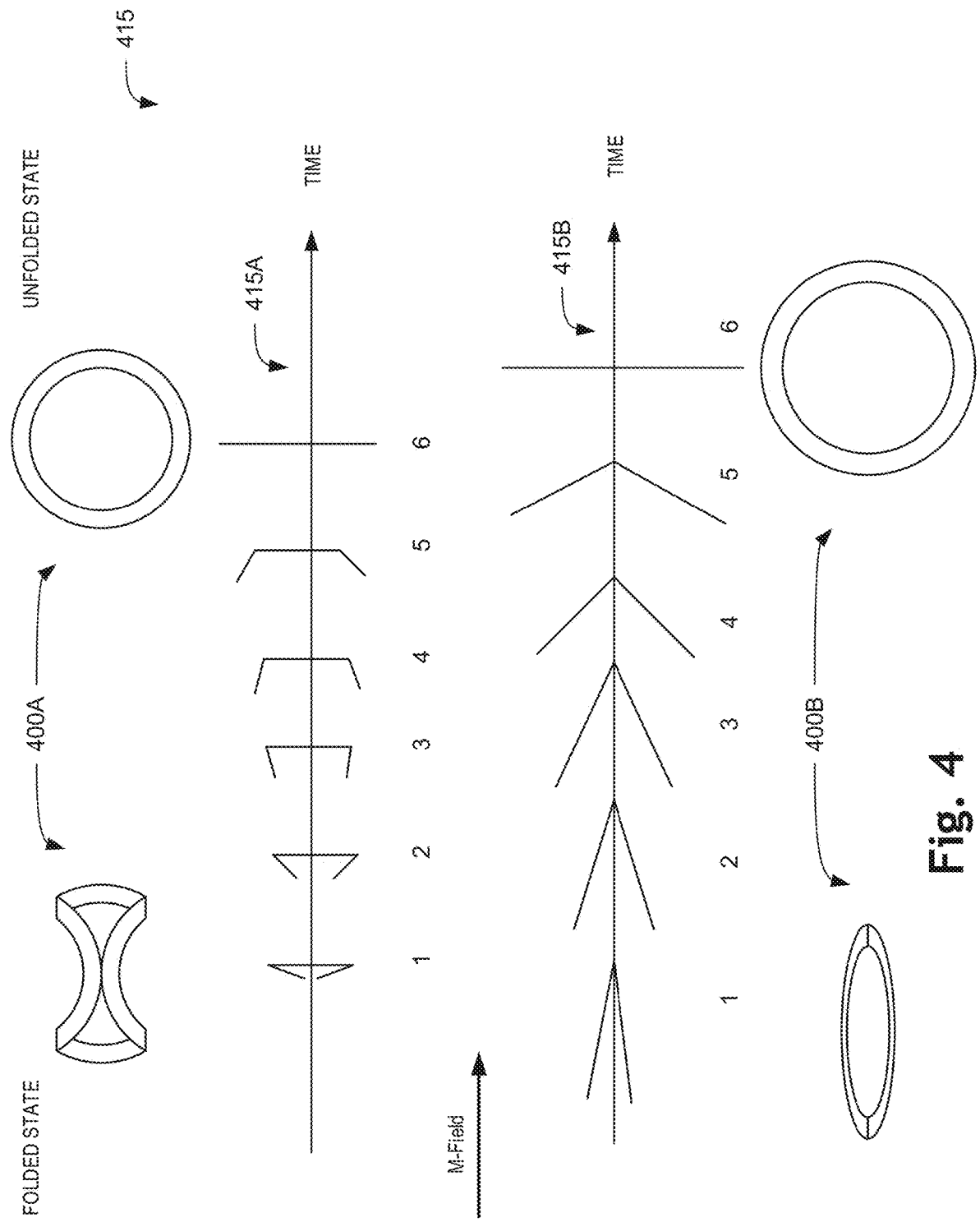
FIG. 4 is an illustration of an unfolding sequence 415 of an IOL in accordance with an embodiment of the present disclosure.

FIG. 4 is an illustration of an unfolding sequence 415 of an IOL in accordance with an embodiment of the present disclosure. The unfolding sequence 415 illustrates unfolding of IOLs 400A and 400B. The IOL 400A has two bends, whereas the IOL 400B has only one bend. The unfolding sequence 415 depicts the IOLs 400A and 400B starting in a folded state and progressing to an unfolded state via a plurality of stages. The stages occur at different times. While the unfolding sequence 415 shows six stages, the number of stages shown is merely for illustration and are not limiting to the present disclosure.

An electromagnetic field or a time dependent magnetic field (M-field) is directed toward the folded IOLs 400A and 400B and is arranged so that the magnetic lines of force extend through the opening of the SMA rings of the IOLs. In some embodiments, the time dependent magnetic field, e.g., the magnetic field, may be near perpendicular to the folded SMA ring. As such, the magnetic field may interact with the IOLs 400A and 400B, which may generate electric current within their respective SMA rings. For example, the magnetic field may propagate through the hole in the center of the SMA rings, which may cause electric current to flow within the SMA rings. The electric current may begin to heat up the SMA rings due to resistive heating. At stage 1, e.g., time 1, the IOLs 400A, B are in the folded state and the M-field may begin interacting with their respective SMA rings. As the power of the M-field is increased or the time duration of the M-field is increased, the current generated in the SMA rings may increase, which may increase the resistive heating. At stage 2, e.g., time 2, the resistive heating may have increased passed a starting transition temperature so that the SMA rings, and by extension the IOLs 400A and 400B, begin to unfold. At each successive stage, e.g., stages 3 through 6, the SMA ring of each IOL increases in temperature due to the inductive heating until a final transition temperature is obtained. At the final transition temperature, the SMA rings may have reached their final geometry and will cease unfolding.

The magnetic field may be provided by various magnetic field generating sources, such as an inductive coil, a Helmholtz coil, etc., which may provide induction power based on a level of power driving the inductive coil. To control the rate of temperature increase of the IOLs 400A and 400B, the amount of power provided to the magnetic field generating source may be adjusted accordingly. The power may be provided in a manner that limits the amount of heat transmitted to the eye, such as in pulsed or modulated manner.

Figure 5:
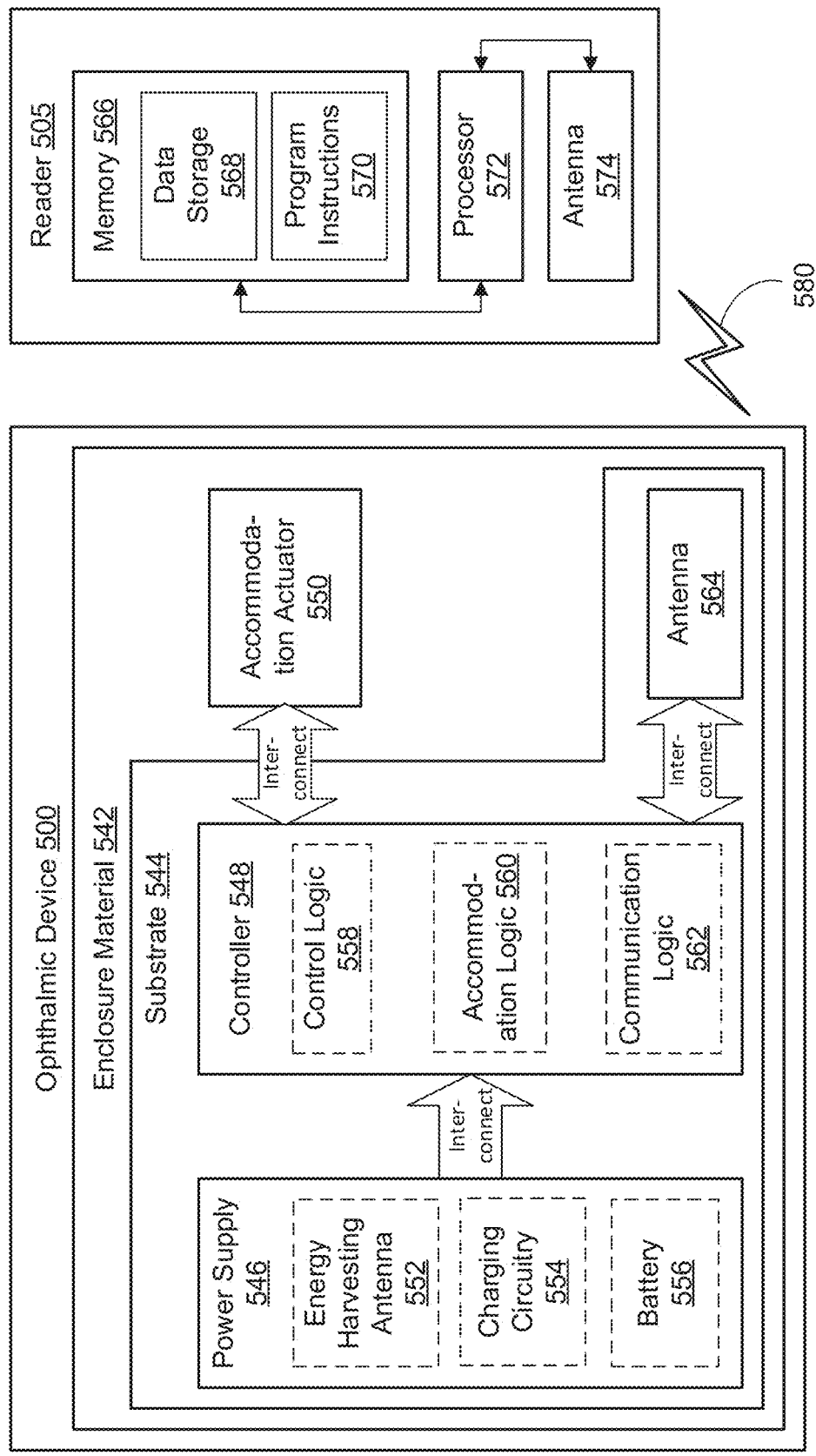
FIG. 5 is a functional block diagram of an IOL 500 with an embodiment of the present disclosure.

FIG. 5 is a functional block diagram of an IOL 500 with an embodiment of the present disclosure. IOL 500 may be an implantable device. In the depicted embodiment, IOL 500 includes a substrate 544 that provides a mounting surface for a power supply 546, a controller 548, an antenna 564, and various interconnects. In some embodiments, the substrate 544 may be one implementation of SMA ring. However, the SMA ring may be included in the IOL 500 in ways discussed above. Alternatively, the substrate 544 may be an implementation of the support structure 102. The illustrated embodiment of power supply 546 includes an energy harvesting antenna 552, charging circuitry 554, and a battery 556. The illustrated embodiment of controller 548 includes control logic 558, accommodation logic 560, and communication logic 562.

Power supply 546 supplies operating voltages to the controller 548 and/or the accommodation actuator 550, which is an example of the dynamic optic 112 and/or 212. Antenna 564 is operated by the controller 548 to communicate information to and/or from IOL 500. In the illustrated embodiment, antenna 564, controller 548, power supply 546, and at least part of the accommodation actuator 550, e.g., an oil electrode, are disposed on/in substrate 544. The other part of the accommodation actuator 550, e.g., a saline electrode, may be disposed elsewhere within the eye, but may be in electrical communication with the controller 548. However, in other embodiments, the various pieces of circuitry and devices contained in ophthalmic device 500 may be disposed in/on substrate 544 or on a separate substrate, depending on the specific design of ophthalmic device 500. For example, in one embodiment, additional control circuitry may be disposed on a separate substrate, which may be implanted in a different part of the eye, such as the sclera.

Substrate 544 includes one or more surfaces suitable for mounting controller 548, power supply 546, and antenna 564. Substrate 544 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 544 to form circuitry, electrodes, etc. For example, antenna 564 can be formed by depositing a pattern of gold or another conductive material on substrate 544. Similarly, interconnects can be formed by depositing suitable patterns of conductive materials on substrate 544. A combination of resists, masks, and deposition techniques can be employed to pattern materials on substrate 544. Substrate 544 can be a relatively rigid material, such as polyethylene terephthalate (PET) or another material sufficient to structurally support the circuitry and/or electronics within enclosure material 542. IOL 500 can alternatively be arranged with a group of unconnected substrates rather than a single substrate 544. For example, controller 548 and power supply 546 can be mounted to one substrate 544, while antenna 564 is mounted to another substrate 544 and the two can be electrically connected via interconnects. Alternatively, the substrate 544 may be a soft, malleable material that the various electronics discussed herein are embedded within, and which may be disposed on one or more surfaces of another mechanical support structure, such as an SMA ring or polyimide-based ring.

Substrate 544 can be shaped as a flattened ring with a radial width dimension sufficient to provide a mounting platform for the embedded electronic components. Substrate 544 can have a thickness sufficiently small to allow substrate 544 to not adversely influence the profile and/or volume of IOL 500. Substrate 544 can have a thickness sufficiently large to provide structural stability suitable for supporting the electronics mounted thereon.

In the illustrated embodiment, power supply 546 includes a battery 556 to power the various embedded electronics, including controller 548. Battery 556 may be inductively charged by charging circuitry 554 and energy harvesting antenna 552. In one embodiment, antenna 564 and energy harvesting antenna 552 are independent antennae, which serve their respective functions of energy harvesting and communications. In another embodiment, energy harvesting antenna 552 and antenna 564 are the same physical antenna that are time shared for their respective functions of inductive charging and wireless communications with reader 505. Additionally or alternatively, power supply 546 may include a photovoltaic cell to capture energy from incoming ultraviolet, visible, and/or infrared radiation. Furthermore, an inertial power scavenging system can be included to capture energy from ambient vibrations.

Charging circuitry 554 may include a rectifier/regulator to condition the captured energy for charging battery 556 or directly power controller 548 without battery 556. Charging circuitry 554 may also include one or more energy storage devices to mitigate high frequency variations in energy harvesting antenna 552. For example, one or more energy storage devices (e.g., a capacitor, an inductor, etc.) can be connected to function as a low-pass filter.

Controller 548 contains logic to choreograph the operation of the other embedded components. Control logic 558 controls the general operation of IOL 500, including providing a logical user interface, power control functionality, etc. Accommodation logic 560 includes logic for receiving signals from sensors monitoring the orientation of the eye, determining the current gaze direction or focal distance of the user, and manipulating accommodation actuator 550 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 562 provides communication protocols for wireless communication with reader 505 via antenna 564. In one embodiment, communication logic 562 provides backscatter communication via antenna 564 when in the presence of an electromagnetic field 580 output from reader 505. In one embodiment, communication logic 562 operates as a smart wireless radio-frequency identification (RFID) tag that modulates the impedance of antenna 564 for backscatter wireless communications. The various logic modules of controller 548 may be implemented in software/firmware executed on a general purpose microprocessor, in hardware (e.g., application specific integrated circuit), or a combination of both.

IOL 500 may include various other embedded electronics and logic modules. For example, a light source or pixel array may be included to provide visible feedback to the user. An accelerometer or gyroscope may be included to provide positional, rotational, directional or acceleration feedback information to controller 548.

The illustrated embodiment also includes reader 505 with a processor 572, an antenna 574, and memory 566. Memory 566 in reader 505 includes data storage 568 and program instructions 570. As shown reader 505 may be disposed outside of IOL 500, but may be placed in its proximity to charge IOL 500, send instructions to IOL 500, and/or extract data from IOL 500. In one embodiment, reader 505 may resemble a conventional contact lens holder that the user places IOL 500 in at night to charge, extract data, clean the lens, etc.

External reader 505 includes an antenna 574 (or group of more than one antennae) to send and receive wireless signals 580 to and from IOL 500. External reader 505 also includes a computing system with a processor 572 in communication with a memory 566. Memory 566 is a non-transitory computer-readable medium that can include, without limitation, magnetic disks, optical disks, organic memory, and/or any other volatile (e.g., RAM) or non-volatile (e.g., ROM) storage system readable by the processor 572. Memory 566 can include a data storage 568 to store indications of data, such as data logs (e.g., user logs), program settings (e.g., to adjust behavior of IOL 500 and/or external reader 505), etc. Memory 566 can also include program instructions 570 for execution by processor 572 to cause the external reader 505 to perform processes specified by the instructions 570. For example, program instructions 570 can cause external reader 505 to provide a user interface that allows for retrieving information communicated from IOL 500 or allows transmitting information to IOL 500 to program or otherwise select operational modes of IOL 500. External reader 505 can also include one or more hardware components for operating antenna 574 to send and receive wireless signals 580 to and from IOL 500.

External reader 505 can be a smart phone, digital assistant, or other portable computing device with wireless connectivity sufficient to provide the wireless communication link 580. External reader 505 can also be implemented as an antenna module that can be plugged into a portable computing device, such as in an embodiment where the communication link 580 operates at carrier frequencies not commonly employed in portable computing devices. In some instances, external reader 505 is a special-purpose device configured to be worn relatively near a wearer's eye to allow the wireless communication link 580 to operate with a low power budget. For example, the external reader 505 can be integrated in a piece of jewelry such as a necklace, earing, etc. or integrated in an article of clothing worn near the head, such as a hat, headband, etc.

Figure 6:
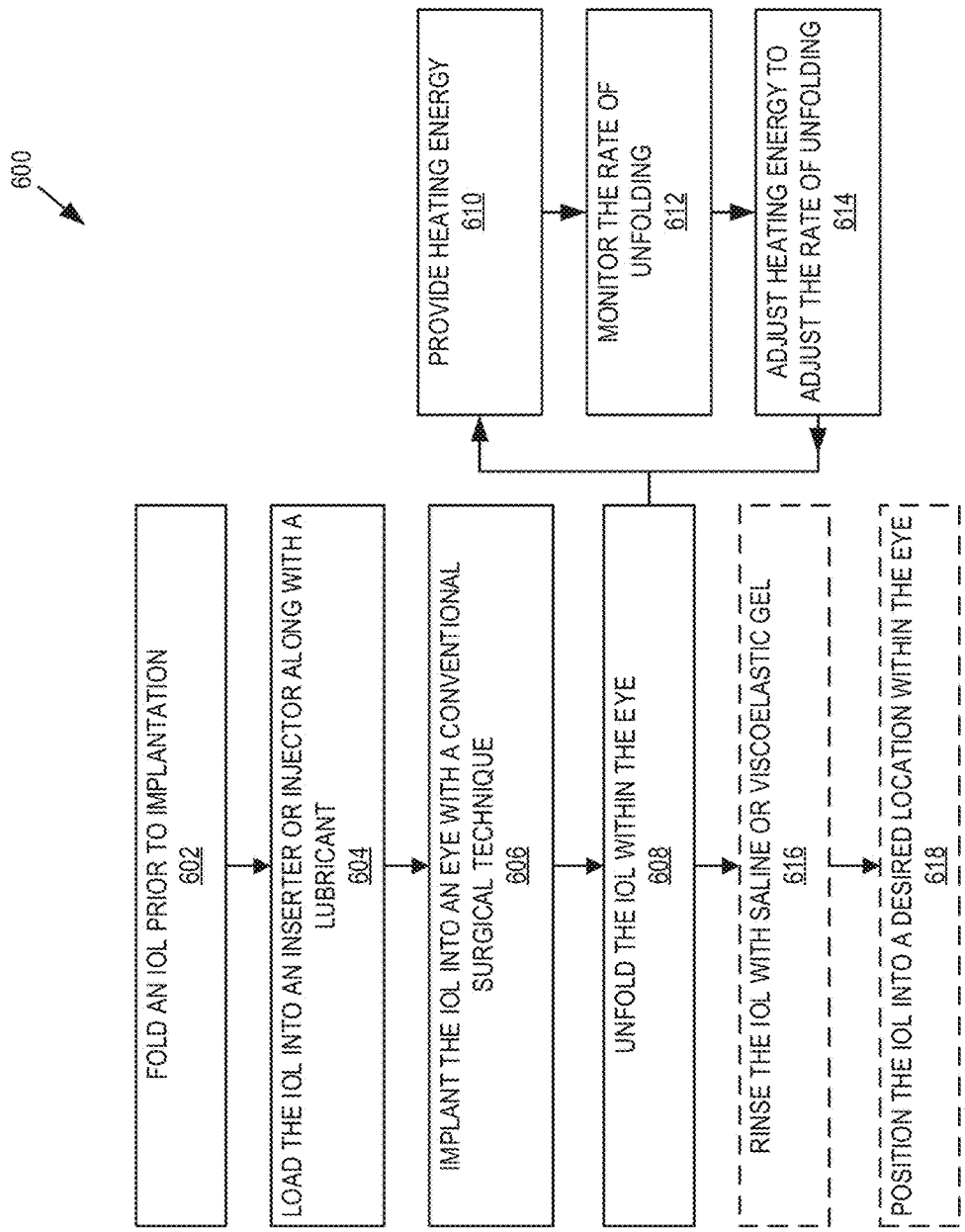
FIG. 6 is an example IOL implantation process 600 in accordance with an embodiment of the present disclosure.

FIG. 6 is an example IOL implantation process 600 in accordance with an embodiment of the present disclosure. The process 600 is an example process for implanting an unfolding an IOL, such as the IOL 100, 200, and/or 400. The process 600 may be performed by an eye care physician. In contrast to implanting a conventional IOL, the implantation of an IOL in accordance with the present disclosure includes the steps of providing a heating energy to unfold in the IOL in a controlled and slow manner while monitoring the unfolding action.

The process 600 may begin at process block 602 with folding an IOL prior to implantation. For example, an IOL may be folded or rolled to reduce its size and prepare it for insertion into the eye. Additionally, the IOL may include an SMA ring that is of a composition that has a transition temperature above body temperature so that the unfolding process can be controlled by the physician as discussed herein. The process block 602 may be followed by the process block 604, which includes loading the IOL into an inserter or injector. Along with loading the IOL into the inserter/injector, one or more lubricants may also be applied to the IOL and or the inserter/injector. In some embodiments, the act of loading the IOL into the inserter/injector may result in the folding and/or rolling of the IOL.

Process block 604 may be followed by process block 606, which includes implanting the IOL into an eye with any conventional surgical technique. The IOL may be implanted into any desirable location of the eye, such as the posterior chamber, anterior chamber, or the secular bag. For example, a small incision, 2 to 5 mm, may be made in the eye, and another in the capsular bag. Using the injector, to continue the example, the rolled and/or folded IOL may be inserted through the incisions and implanted into the capsular bag. It should be noted that the crystalline lens material that was in the capsular bag may be removed before the IOL is implanted.

Process block 606 may be followed by process block 608, which includes unfolding the IOL within the eye. The IOL may, for example, be unfolded/unrolled into a desired geometry. The unfolding of the IOL may include heating of the IOL, monitoring a rate of unfolding, and adjusting the heating of the IOL to maintain a slow and controlled unfolding. For example, within the process block 608, the process steps of providing heating energy (process block 610), monitoring a rate of unfolding (process block 612), and adjusting the heating energy to adjust the rate of unfolding (process block 614) may be included.

The heating energy of the process block 610 may be provided through induction heating by placing an induction coil close to the eye with the IOL. Alternatively, the induction heating may be provided as laser pulses, ultrasound, or electric heating. Induction power may generate electric current in an SMA ring of the IOL, which may cause the SMA ring to heat up due to resistive heating. As the temperature of the SMA ring increases past a starting transition temperature, the SMA ring may begin to unfold at a rate based on the rate of temperature increase. The rate of temperature increase may be based on the induction power increase, but may also be affected by the heat capacitance of the SMA ring and the thermal conduction by the IOL to the surrounding intraocular liquid. As the IOL unfolds, the implanting physician may monitor the rate of unfolding (process block 612), and adjust the induction power (process block 614) accordingly. For example, if the IOL is unfolding faster than desired, the physician may decrease the induction power to slow the temperature increase of the SMA ring. Alternatively, if the IOL is unfolding slower than desired, the induction power may be increased to increase the rate of unfolding. The physician may continue to provide the heating energy, e.g., induction energy, to the IOL until a final transition temperature of the SMA ring is obtained. By heating the SMA ring to the final transition temperature, the phase of the SMA ring may completely change to the austenite phase from the martensite phase, and may be in a completely unfolded geometry. After unfolding, the SMA ring will stay in the desired geometry and provide strength to the IOL.

The process block 616 may optionally follow the process block 608 with rinsing the IOL with saline or viscoelastic gel. The rinsing of the IOL post implantation may be performed to remove any debris and left over crystalline material from the capsular bag, for example. Upon completion of the rinsing step, the saline or viscoelastic gel used for the rinse may remain in the capsular bag. The remaining fluid, however, may slowly be replaced by the eye's aqueous humor.

The process block 616 may optionally be followed by the process block 618, which includes positioning the IOL into a desired location within the eye. For example, the IOL may be positioned into the ultimate location for utility, e.g., providing vision correction and accommodation for the user. The positioning may include finely positioning the optical axis of the optical window, such as the optical window 110, to be in line with and parallel with the optical axis of the eye. The positioning of the IOL may be an iterative process and may include sequential minor adjustments and observations by the physician to obtain the desired position. It should be noted that process block 618 may be continually performed and/or periodically performed during process blocks 606 through 614.

The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel.

Figure 7:
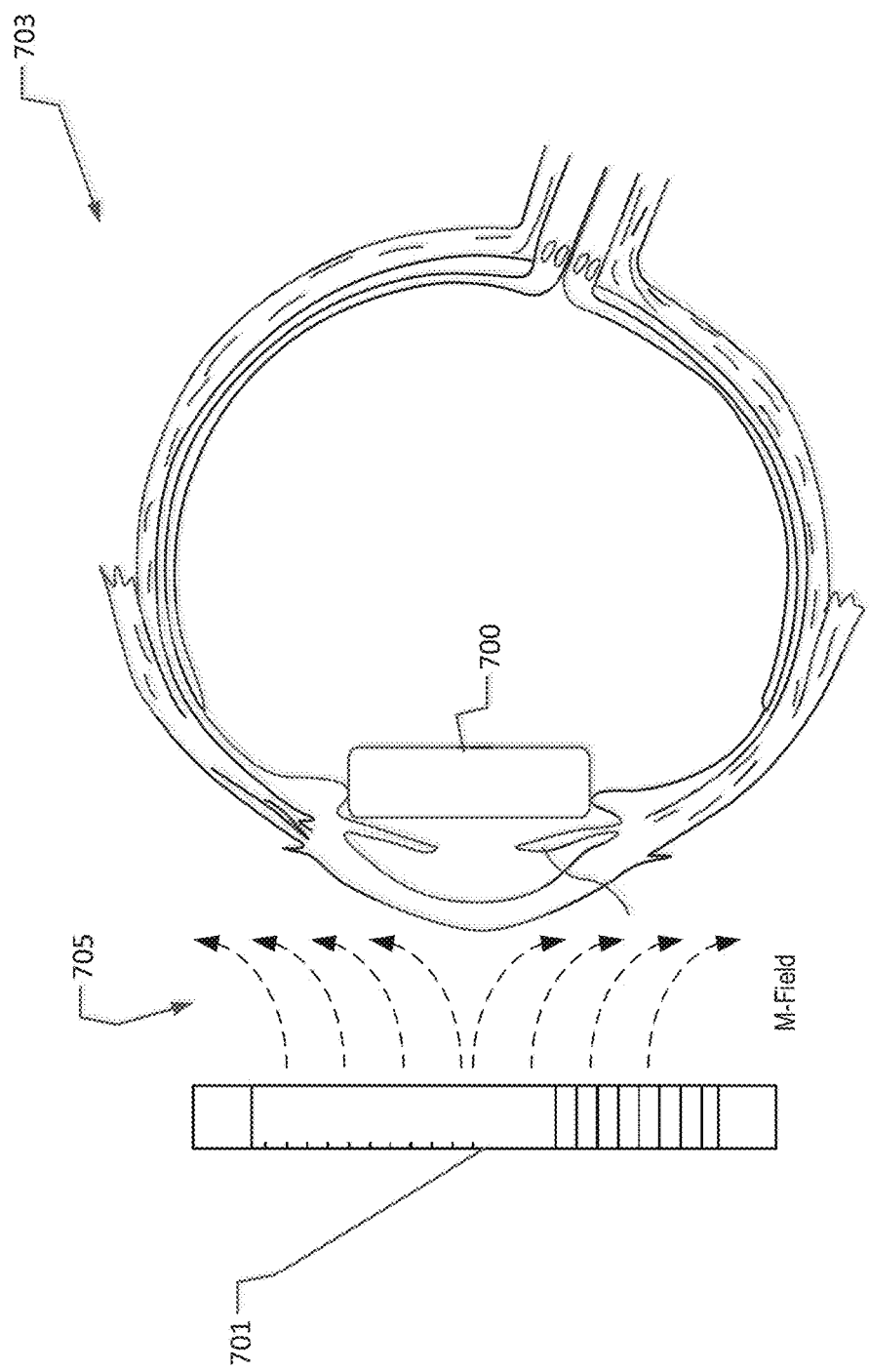
FIG. 7 is an illustration of an arrangement 703 for providing heating energy to an implanted IOL in accordance with an embodiment of the present disclosure.

FIG. 7 is an illustration of an arrangement 703 for providing heating energy to an implanted IOL in accordance with an embodiment of the present disclosure. The arrangement 703 illustrates the use of an inductive coil 701 providing inductive energy to an implanted IOL 700. The inductive coil 701 may be a small hand held or mounted wand used to provide the inductive energy 705 to the implanted IOL 700. While only a few lines of force are shown for inductive energy 705, the inductive energy 705 will extend into the eye and through the IOL and the SMA ring of the IOL to cause resistive heating of the SMA ring. In some embodiments, the inductive coil 701 may have a center opening that allows the treating physician to monitor the IOL 700 while controlling the inductive energy 705. Having the ability to monitor the IOL 700 during unfolding may allow the treating physician to adjust the inductive power to either speed up or slow down the unfolding process, as discussed in FIG. 6.

Alternatively, a Helmholtz coil may be used as the inductive coil 701. A Helmholtz coil, which may include a large conductive hoop placed in front of a person's head and another placed behind, may provide the treating physician with more flexibility in monitoring the unfolding process and in having access to the user's eye. Further, the Helmholtz coil may provide a more uniform magnetic field across the IOL 700, which may provide a more uniform and controlled unfolding process. Of course, other means for providing the inductive energy are also possible and are within the bounds of the present disclosure.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for the controlled unfolding of an intraocular lens (IOL), the method comprising:
    inserting a folded IOL into an eye, wherein the IOL includes a shape memory alloy (SMA) ring having a transition temperature above a body temperature; and
    heating the SMA ring to a temperature that is at least to the transition temperature, wherein the heating causes the SMA ring to unfold the IOL.

2. The method of claim 1, wherein heating the SMA ring to a temperature that is at least the transition temperature includes:
    inductively heating the SMA ring to at least the transition temperature.

3. The method of claim 2, wherein the inductive heating is provided by an inductive coil.

4. The method of claim 2, wherein the inductive heating is provided by a Helmholtz coil.

5. The method of claim 1, further comprising:
    monitoring the unfolding of the IOL during the heating of the SMA ring to determine a rate of unfolding; and
    adjusting a rate of the heating of the SMA ring in response to the monitoring.

6. The method of claim 5, wherein adjusting the heating of the SMA ring in response to the monitoring includes:
    to increase the rate of the unfolding, increasing the rate of the heating.

7. The method of claim 6, wherein adjusting the heating of the SMA ring in response to the monitoring includes:
    to decrease the rate of unfolding being above a threshold, decreasing the rate of the heating.

8. The method of claim 1, wherein the SMA ring is embedded in a support structure of the IOL.

9. The method of claim 1, wherein the SMA ring is embedded in a sidewall of the IOL.

10. The method of claim 9, wherein the SMA ring is an electrode of the IOL.

11. The method of claim 1, wherein the SMA ring is an antenna of the IOL.

12. The method of claim 1, further comprising:
    folding the IOL into a desired geometry; and
    loading the folded IOL into an inserter or injector for implantation.

13. The method of claim 12, wherein the folding of the IOL is performed at a temperature below the transition temperature.

14. The method of claim 12, wherein the folding of the IOL is performed at a temperature above the transition temperature.

15. The method of claim 1, further comprising:
    after unfolding the IOL, rinsing the IOL with a saline or viscoelastic gel; and
    adjusting a position of the IOL in the eye.

16. The method of claim 1, wherein heating the SMA ring includes:
    heating the SMA ring from a starting transition temperature to a final transition temperature, wherein the SMA ring is completely unfolded when the temperature reaches the final transition temperature.

17. The method of claim 1, wherein heating the SMA ring to a temperature that is at least the transition temperature includes:
    heating the SMA ring to at least the transition temperature using one of laser pulses, ultrasound, or warm saline.

18. A method of unfolding an intraocular lens (IOL), the method comprising:
    implanting a folded IOL into an eye, wherein the IOL includes a support structure and a shape memory alloy (SMA) ring included in the support structure, the SMA ring having a transition temperature above body temperature; and
    inductively heating the SMA ring to a temperature that is at least to the transition temperature, wherein the heating causes the SMA ring to unfold the IOL.

19. The method of claim 18, wherein inductively heating the SMA ring to a temperature that is at least to the transition temperature comprises:
    inductively heating the SMA ring from a starting transition temperature to a final transition temperature, wherein the SMA ring is completely unfolded when the temperature reaches the final transition temperature.

20. The method of claim 18, wherein the inductive heating is provided by an inductive coil.

21. The method of claim 18, wherein the inductive heating is provided by a Helmholtz coil.

22. The method of claim 18, further comprising:
    monitoring the unfolding of the IOL during the heating of the SMA ring to determine a rate of unfolding; and
    adjusting the heating of the SMA ring in response to the monitoring.

23. The method of claim 22, wherein adjusting the heating of the SMA ring in response to the monitoring includes:
    to increase the rate of unfolding, increasing the heating to increase a rate of unfolding.

24. The method of claim 22, wherein adjusting the heating of the SMA ring in response to the monitoring includes:

to decrease the rate of unfolding, decreasing the heating to decrease a rate of unfolding.

* * * * *